United States Patent

Johannsen et al.

Patent Number: 5,708,123
Date of Patent: Jan. 13, 1998

[54] ELECTROACTIVE MATERIALS, A PROCESS FOR THEIR PREPARATION AS WELL AS THE USE THEREOF

[75] Inventors: Ib Johannsen, Værløse; Mikkel Jørgensen, Brøndby, both of Denmark

[73] Assignee: NKT Research Center A/S, Brondby, Denmark

[21] Appl. No.: 553,691

[22] PCT Filed: Jun. 9, 1994

[86] PCT No.: PCT/DK94/00225

§ 371 Date: Jun. 26, 1996

§ 102(e) Date: Jun. 26, 1996

[87] PCT Pub. No.: WO94/29314

PCT Pub. Date: Dec. 22, 1994

[30] Foreign Application Priority Data

Jun. 11, 1993 [DK] Denmark .................. 0685/93

[51] Int. Cl.$^6$ .................................. C08G 12/00
[52] U.S. Cl. .................. 528/229; 528/228; 528/125; 528/127; 528/128; 544/179; 544/224; 544/336; 544/338; 544/342; 544/344
[58] Field of Search ........................ 528/229, 228, 528/125, 127, 128; 544/179, 224, 336, 338, 342, 344

[56] References Cited

U.S. PATENT DOCUMENTS 4,184,751  1/1980  Nicholson .................. 350/357

FOREIGN PATENT DOCUMENTS 0 032 991  8/1981  European Pat. Off. .......... G02F 1/17
0 240 226  10/1987  European Pat. Off. .......... G02F 1/17
2 166 148  4/1986  United Kingdom ............ C09B 19/00

OTHER PUBLICATIONS

Bange et al., "Electrochromic Materials for Optical Switching Devices", *Advanced Materials*, 1990, pp. 10–16.
Nomura et al., "Electrochemical and Electrochromic of Polymer Complex Films Composed of Polytetramethyleneviologen and Poly[p–Styrenesulfonic Acid] Containing a Conductive Powder", *J. Macromol. SCI–CHEM.*, A26(2&3), 1989, pp. 593–608.

*Primary Examiner*—Duc Truong
*Attorney, Agent, or Firm*—Cushman Darby & Cushman IP Group of Pillsbury Madison & Sutro LLP

[57] ABSTRACT

Stable, electroactive material which when a potential is applied from the outside is subjected to one or more reversible redox reactions, for use in devices with an electrochromic display or another electrochromic color change or in batteries.

The material comprises a condensed ring structure, the oxidized form of which is of the formula

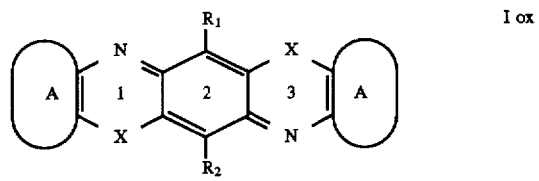

in which $R_1$, $R_2$, X, and A may have any meaning with the proviso that the condensed ring structure maintains the reversible properties.

The material can be prepared by various processes and it is suited for use as electrochromic material for use in devices with an electrochromic display or as coating on windows because it presents a distinct and easily visible color change when it is subjected to a potential. In addition, the material is suited for use in rechargeable batteries because is possesses an excellent capacity and reversibility.

11 Claims, 2 Drawing Sheets

ELECTROACTIVE MATERIALS, A PROCESS FOR THEIR PREPARATION AS WELL AS THE USE THEREOF

This application claims benefit of international application PCT/DK94/00225, filed Jun. 9, 1994.

TECHNICAL FIELD

The present invention relates to a stable, electroactive material which when a potential is applied from the outside is subjected to one or more reversible redox reactions, for use in devices with an electrochromic display or another electrochromic colour change or in batteries, and to a process for the preparation of the stable, electroactive material with a single, reversible, redox-active condensed ring structure or in form of an oligomeric or polymeric material containing several such redox-active condensed ring structures.

The electroactive material according to the invention can be an electrochromic material of the type changing colour by one or more reversible redox reactions. The invention relates also to the use of such electrochromic materials in devices with an electrochromic display or as coating on windows.

The invention relates in addition to the use of the stable electroactive materials in rechargeable batteries.

BACKGROUND ART

Elektrochromism refers to a special property of particular materials, subsequently referred to as electrochromic materials, which in a reversible manner can change colour (spectral absorption and/or reflection) as a reaction to a potential applied from the outside.

Electrochromic materials can be widely used as they for instance can be used for electrochromic display for use in light signs or another display use where it is possible in no time to change showcards, to display "today's special" or the like. Electrochromic materials can also be used in form of window coatings allowing a subduing of the sunlight as required. In order to illustrate in greater detail the use of electrochromic materials in devices with an electrochromic display reference can for instance be made to an article by K. Bange and Th. Gambke "Electrochromic Materials for Optical Switching Devices", Adv. Mater. 2 (1990) No. 1, pages 10 to 16, as well as to U.S. Pat. No. 4,184,751 (Nicholson).

Numerous inorganic and organic electrochromic materials are known, among which the best tested and most used electrochromic material is wolframtrioxide $WO_3$ displaying a cathodic coloration. Other electrochromic materials based on a cathodic coloration are for instance $MOO_3$, $V_2O_5$, $Nb_2O_5$, and $TiO_2$. Oxides of irridium, rhodium, nickel, and cobalt displaying an aniodic coloration can also be mentioned. Among the organic electrochromic materials viologenes can be mentioned, viz. dialkyl derivatives of 4,4'-bipyridinium salts, pyrazoline, pyridine, the tetrathiafulvalene system, and organometallic compounds, such as complexes of metal and diphthalocyanine. Polyaniline can furthermore be mentioned. The advantages of the organic electrochromic materials are their fast conversion capacity and their simple handling in the construction of electrochromic devices. An undesired and irreversible side effect of the weakly bound hydrogen ions and nitrogen ions is, however, one of the commonly known drawbacks of organic electrochromic materials as such side effects cause short lives and a poor stability to ultraviolet light.

EP Publication No. 32 991 (Engler et al.) discloses an electrochromic material in form of a polymer resin, to which electroactive molecules are covalently bonded and in which a non-electroactive ionic salt is incorporated. The object of the latter material is to improve the switching speed and the stability of the electrochromic material. These known materials present, however, still a poor stability. In addition, a rather indistinct change of colour appears, which is probably due to the structure of the materials, said structure not providing sufficient hindrance of interactions between the individual redox active units.

Nomura et al., J. Macromol. Sci.-Chem., A26 (2 & 3), pages 593 to 608 (1989) discloses an electrochromic material in form of a polymer complex between electrochromic polytetramethylene viologene (PVT) and poly(p-styrene sulphonic acid) (PSS).

This PTV/PSS polymer complex has, however, a low conductivity and must therefore be used in combination with a conductive powder as a composite. The conductive powder is a mixture of $TiO_2$ and $SnO_2$ admired $SbO_2$. The addition of the conductive powder is, however, disadvantageous in making the electrochromic material opaque, which deteriorates the electrochromic display and limits the use of the material for reflective display.

Thus a demand exists for an improved electrochromic material encumbered with the advantageous capacity of fast colour changes, such as it is known in connection with conventional organic electrochromic materials, which is easy to handle, and which is encumbered with an improved stability to light and other physical or chemical effects.

A demand also exists for a stable electroactive material, which, when an external potential is applied, is subjected to a reversible redox reaction in such a manner that the material is suited for use in rechargeable batteries.

BRIEF DESCRIPTION OF THE INVENTION

The above demands are met by a stable, electroactive material, which when a potential is applied from the outside is subjected to one or more reversible redox reactions, for use in devices with an electrochromic display or another electrochromic colour change or in batteries, said material being characterised by containing at least one condensed ring structure I of one of the formulas I red or I ox in the redox reaction equation:

in which the groups X, which may be identical or different, are O, S or $NR_3$, where the structures A, which may be identical or different, may be any molecular structure not blocking the redox reaction, and, if desired, may carry one or more identical or different substituents $R_4$, where $R_1$, $R_2$, $R_3$, and $R_4$, which may be identical or different, may be any substituent not blocking the redox reaction, and where one or more of the substituents $R_1$, $R_2$, $R_3$, and $R_4$ may also form part of a linker residue L, which is attached to one or more additional ring structures I, and where L is a divalent or polyvalent group not blocking the redox reaction.

The electroactive material according to the invention is remarkable for possessing a high chemical stability which also involves a high photochemical stability. The material can in a simple manner be modified such that it for instances can form part of a polymer, and accordingly the material can be dissolved in organic solvents and shaped by conventional dipping and printing techniques. The material according to the invention deviates in this respect from electrochromic materials based on inorganic electrochromic materials, and from most organic electrochromic materials, such as phthalocyanines, which can only be applied in form of coatings by methods involving a high vacuum and/or high temperatures.

The electroactive materials according to the invention are advantageously prepared in form of an oligomer or polymer by simple polymerisation processes, either before or during the coating process, which allows a high design freedom concerning the preparation of the final electroactive laminate for use in conventional devices, such as devices for electrochromic display or as window coatings.

A further advantage of the electroactive materials according to the invention is that both the oxidized molecular structure of the formula I ox and the reduced (coloured) structure of the formula I red include filled electron band structures. The resulting stability is very high compared to other electrochromic systems where the coloured state is characterised by being a radical, i.e. a structure with a single unpaired electron in the outer electron band structure. As it is known, radicals are very reactive compounds with a tendency to react with other substances, such as present oxygen or water, which results in an irreversible decomposition. This drawback is for instance found in viologen-based dyes.

The material is conductive per se to a certain extent, and accordingly it is not necessary to add a conductive powder as suggested in the previously mentioned article by Nomura et al. in order to ensure the necessary conductivity. The stable electroactive material according to the invention presents typically a specific resistance lower than $10^9$ ohm·cm.

The high stability of the material according to the invention renders it suited for use also in rechargeable batteries, because in such batteries it is possible to obtain a significant accumulation of the charge in layers of material produced from the electroactive material according to the invention.

The scope of the applicability of the invention appears from the following detailed explanation. It should, however, be underlined that the detailed explanation and the specific Examples merely illustrate preferred embodiments of the invention, as various alterations and modifications can be carried out within the scope of the invention and are obvious to persons skilled in the art in view of the detailed explanation.

DETAILED DESCRIPTION OF THE INVENTION

The molecular structures A can in principle be any molecular structure meeting the decisive condition that they have no blocking effect on the reversible redox reaction.

Typical molecular structures A are ring structures condensed with ring 1 and ring 3, respectively, in the ring structure of the general formula I.

Thus A can typically consist of or comprise a 5 or 6-linked ring structure optionally containing one or more, especially one or two hetero atoms selected among N, O, and S, preferably such being of an aromatic structure.

Examples of such ring structures are benzene, thiophene, pyrrole, furan, thiazole, pyridine, pyrimidine, imidazole, pyrazole, pyradazine, and pyrazine.

Further examples of ring structures A are ring structures of the above type which are condensed with one or more additional rings, especially 5 or 6-linked rings selectable among both carbocyclic and heterocyclic rings, and which can also be aromatic, whereby, however, the aromatic character is usually of a minor importance for the rings not directly condensed with ring 1 or ring 3.

Examples of ring structures A including at least one ring beyond the one condensed with ring 1 or ring 3 are naphthalene, anthracene, phenanthrene, indole, isoindole, indanzole, isoquinoline, quinoline, quinazoline, quinoxaline, phthalazine, phtheridine, benzofuran, and isobenzofuran.

Ring structures A can be unsubstituted or they can be substituted with one or more, for instance from 1 to 6, such as 1 to 4 substituents, $R_4$, which can be identical or different. Such substituents are again subject to the criteria that they must not block the reversible redox reaction.

Both the substituents $R_4$ and the substituents $R_1$, $R_2$, and $R_3$ are subject only to the criteria that they must not block the reversible redox reaction.

The substituents $R_1$, $R_2$, $R_3$, and $R_4$ can advantageously be utilized for adapting the properties of the molecular structure of formula I, such as for adapting the solubility especially in organic solvents, such as tetrahydrofuran, chloroform or toluene, in such a manner that the material is easily applied onto a carrier material.

Examples of substituents $R_1$, $R_2$, $R_3$, and $R_4$ ensuring the desired solubility are straight chained and branched chains with 1 to 24 chain atoms selected among C, O, N, S, and Si, such as alkyl with 1 to 18 carbon atoms, thioalkyl with 1 to 18 carbon atoms and 1 to 6 sulphur atoms, oxoalkyl with 1 to 18 carbon atoms and 1 to 6 oxygen atoms, as well as alkenyl with 1 to 18 carbon atoms, and these groups can, if desired, contain inactive or reactive substituents. Chain groups with carboxyl groups or carboxyl derivative groups can for instance be used, where these groups can be utilized in connection with incorporation of the molecular structure I in a polymeric material.

The substituents $R_1$, $R_2$, $R_3$, and $R_4$ can also be selected in order to change the electrochemical properties. Thus it is possible by means of either electronegative substituents, such as halogen, nitro or cyano, or electropositive substituents, such as hydroxy, alkoxy or alkylamino, to move the absorption spectra towards lower or higher wavelengths, respectively.

According to a particularly attractive embodiment, the individual electroactive units are bonded together in chains by means of linker units with the effect that oligomeric or polymeric structures are formed. The use of flexible linker units results in good properties facilitating the producing processes in which the stable, electroactive materials according to the invention are used, and good film-forming properties are obtained. Correspondingly, a polymeric structure renders it possible to obtain an improved stability of the final product because the electroactive part of the molecular structure is locked in a structure and cannot therefore diffuse into other layers of a laminate including the material. In this manner it is avoided that the electrochemical efficiency of the product is reduced.

As the molecular structure of the general formula I thus can form part of oligomeric or polymeric structures or molecules, it should be understood that the above examples of meanings of the ring structures A and the substituents $R_1$, $R_2$, $R_3$, and $R_4$ for practical reasons cannot be complete in the present specification and cover all the numerous possibilities within the scope of the present invention. Here, the criteria must, of course, again be that the reversible redox reaction must not be blocked, but may be supported or modified so as to adapt the stable readox-active material to the particular application in question.

The only criteria for the linker units L is that they should not block the reversible redox reaction. Typically, L can be a straight chained or branched, divalent or polyvalent group with 3 to 150, preferably 5 to 20 chain atoms selected amont C, O, N, S, Si.

Typically, such linker units L are pure carbon chains or polyether chains of the formula where $(x+1)\cdot m + y = 3$–150, or silicones for instance of the formula where $m_1$ is 2 to 75 and R is hydrogen or an organic group.

In electroactive materials according to the invention, the linker residues L are typically of a chain length of from 0.4 to 20 nm.

The use of the stable electroactive materials in dissolved form, for instance for forming coatings, renders it possible to typically use solvents relatively inpolar relative to water, such as halogenated and/or aromatic hydrocarbons.

Examples of electroactive materials according to the invention appear from Tables 1 and 2.

TABLE 1

Example of Compounds of formula I

| Intern. code | X (1) | $R_3$ (1) | X (3) | $R_3$ (3) | $R_1$ | $R_2$ | $R_4$ |
|---|---|---|---|---|---|---|---|
| MJ 42 | N-$R_3$ | cyclohexyl | N-$R_3$ | cyclohexyl | H | H | — |
| MJ 45 | N-$R_3$ | butyl | N-$R_3$ | butyl | H | H | — |
| MJ 46 | N-$R_3$ | hexyl | N-$R_3$ | hexyl | H | H | — |
| MJ 30 | N-$R_3$ | phenyl | N-$R_3$ | phenyl | H | H | — |
| MJ 22 | N-$R_3$ | —(CH$_2$)$_2$—Otosyl | N-$R_3$ | —(CH$_2$)$_2$—Otosyl | H | H | — |

| Intern. code | X (1) | $R_3$ (1) | X (3) | $R_3$ (3) | $R_1$ | $R_2$ | $R_4$ | Position for $R_4$ |
|---|---|---|---|---|---|---|---|---|
| MJ 24 | N-$R_3$ | H | N-$R_3$ | H | H | H | carboxy | 3 |
|  |  |  |  |  |  |  | carboxy | 10 |
| MJ 18 | N-$R_3$ | H | N-$R_3$ | H | H | H | hexylamino | 2 |
| MJ 19 | N-$R_3$ | H | N-$R_3$ | H | H | H | —SO$_2$NHbutyl | 2 |
| MJ 68 | O | — | O | — | Cl | Cl | — |  |
| MJ 71 | O | — | O | — | Cl | Cl | methyl | 2 |
|  |  |  |  |  |  |  | methyl | 9 |
| MJ 72 | O | — | O | — | H | H | methyl | 2 |
|  |  |  |  |  |  |  | methyl | 9 |
| MH 73 | O | — | O | — | H | H | carboxy | 2 |
|  |  |  |  |  |  |  | carboxy | 9 |
| MJ 84 | N-$R_3$ | H | N-$R_3$ | H | H | H | nitro | 3 |
|  |  |  |  |  |  |  | nitro | 10 |
| MJ 2 | N-$R_3$ | H | N-$R_3$ | H | H | H | — |  |
| MJ 3 | N-$R_3$ | H | N-$R_3$ | H | H | H | carboxy | 2 |
| MJ 6 | N-$R_3$ | 2-propenyl | N-$R_3$ | 2-propenyl | H | H | — |  |

TABLE 2

Examples of compounds of formula I

| Internal Code | X   | L |
|---|---|---|
| MJ 28  | N—L | butylene |
| MJ 90  | N—L | —$(CH_2)_3$—O—$(CH_2)_4$—O—$(CH_2)_3$— |
| MJ 91  | N—L | —$(CH_2)_{12}$— |
| MJ 100 | N—L | —$(CH_2)_2$—O—$(CH_2)_2$—O—$(CH_2)_2$— |
| MJ 97  | N—L | —$(CH_2)_2$—O—$(CH_2)_2$—O—$(CH_2)_2$—O—$(CH_2)_2$— |

The electroactive molecular structures of the formula I can be prepared in a number of various ways according to the meanings of the substituents. Below suitable methods are illustrated.

METHOD A

A particularly suited and novel method for preparing the ring structures I is the method A indicated in claim 10 a). Method A is in principle suited for the preparation of any ring structures I. Examples of compounds advantageously prepared by method A are ring structures I, in which X has the meaning $NR_3$. This embodiment is illustrated in Example 3. The quinone of the formula III is typically a 2,5-dimethoxy-quinone or a 2,5-dihydroxyquinone, and preferably a 2,5-dimethoxyquinone is used. The reaction usually employs 2 mol amine of formula II per mol quinone of the formula III. The reaction is performed under slightly acid conditions, such as in the presence of a weak organic acid, such as acetic acid, and the reaction mixture is advantageously heated under reflux.

Method A is also suited for the preparation of 7,14-dioxa-5,12-di-aza-pentacenes, where the starting material used is 2-hydroxyaniline optionally containing one or more $R_4$-substituents, said $R_4$ having the meaning stated in the ring structure I.

METHOD B

A further suited method B for the preparation of a particular group of ring structures Ib being a sub-group of the ring structures I is indicated in claim 10 b). Method B is particularly suited for the preparation of unsymmetrical tetra-aza-pentacenes, i.e. compounds of the formula Ib, in which A bonded to ring 3 is a benzene ring substituted with at least one substituent $R_4$. Example 5 illustrates the preparation of an unsymmetrical tetra-aza-pentacene.

The condensation of the compounds of the formula IV is performed in the presence of an oxidation agent, such as $FeCl_3$ or $CeCl_4$. The resulting compound of the formula V is reacted with an equimolar amount of the compound of the formula VI. This reaction is advantageously performed by using a high-boiling, organic acid as solvent, such as benzoic acid or p-toluene sulphonic acid.

The stable electroactive material according to claim 1 is often present in form of an oligomeric or polymeric material containing several ring structures I linked together by means of linker residues L of the meaning stated in claim 1. Oligomeric or polymeric materials include typically materials composed of repetition units, where the condensed ring structure I forms part of each repetition unit. The number of repetition units n is typically in the range of 5 to 1,000, preferably between 5 to 500. Such oligomeric or polymeric materials can also be prepared in a number of different ways.

METHOD C

A suited method C for the preparation of a particular group of polymerised ring structures Ic being a sub-group of the ring structures I is described in claim 11 c). This method is described in greater detail in the Examples 1 and 6. In the compound used as starting material of the formula VII, the leaving group $Q_2$ can typically be halogen or a sulphonate group, such as mesylate or tosylate or a corresponding leaving group. The nitro groups of the compound of the formula IX are reduced in a conventional manner, such as by means of stannous chloride in acid liquid. The polymerisation degree n is preferably in the range of 5 to 1,000, especially 5 to 500.

METHOD D

Claim 11 d) indicates a suited method D for the preparation of a particular group of ring structures Id, where the polymerisation is performed through the A ring structures.

METHOD E

Claim 11 e) indicates a method E for the preparation of a particular oligomeric or polymeric structure Ie being a sub-group of the ring structures I. By method E, the linking is performed through the X-groups. The reaction is an electrophilic reaction, which, if necessary, can be performed in the presence of a base as catalyst, such as in an aprotic, polar solvent, such as DMF or tetrahydrofuran. Examples of such a base are for instance strong bases, such as butyllithium, NaH, and potassium-t-butoxide. The leaving group $Q_4$ in connection with formula XV can typically be halogen or a sulphonate group, such as metsylate or tosylate, or a corresponding leaving group. The compound of the formula XIV used as starting material by method E falls within the definition of the ring structure I, and such starting materials can advantageously be prepared by means of the above method A. Method B can also be used for preparing compounds of the formula XIV, in which $R_3$ in ring 3 is hydrogen, and in which A bonded to ring 1 is as indicated in the structure Ib.

The following Examples illustrate the invention in greater detail.

EXAMPLE 1 (METHOD C)

The present Example illustrates the preparation of an electrochromic fluoroindine polymer, poly[5,12'-ω-decandiyl-(5,12-dihydro-5,7,12,14-tetraazapentacene)], by the following reaction:

a) N,N'-bis(2-nitrophenyl)-1,12-diaminododecane 34 g (0.216 mol) 2-nitro-chlorobenzene and 20 g 1,12-diaminododecane (0.10 mol) are mixed with 40 g potassium carbonate and 200 ml N,N-dimethylformamide (DMF). The mixture is heated with reflux while subjected to a vigorous stirring for four hours. Subsequently, the inorganic salts are filtered off and washed with a small amount of DMF. The entire DMF-phase is distilled under vacuum to remove substantially all DMF. The remanence is cooled, and 200 ml water are added while vigorously stirred. Subsequently, the water phase is decanted off, and the product is caused to crystallize by the addition of approximately 100 ml ethanol. The crystals are filtered off, washed twice with 25 ml ethanol and 100 ml petroleum ether followed by an air-drying of the product. Yield 21.8 g (49%), melting point 79° to 80° C.

b) N,N'-bis(2-aminophenyl)-1,12-diaminododecane 20 g (0.045 mol) N,N'-bis(2-nitrophenyl)-1,12-diaminododecane are dissolved in 100 ml concentrated hydrochloric acid, and 43 g (0.19 mol) stannochloride dihydrate dissolved in 50 ml concentrated hydrochloric acid are added. The mixtured is heated to approxiately 100° C. while stirred, and after three hours the product separated off is cooled. The water phase is separated off, and the product is suspended in 200 ml hot water, whereafter it is poured into 500 ml 2M sodium hydroxide. The released tetraamine is extracted twice with 150 ml methylchloride, and the organic phase is dried over magnesium sulphate and evaporated, whereby the product is crystallized. Yield 17.30 g (100%), melting point 85° to 88° C.

c) Fluoroindine Polymer: Poly[5,12'-omega-decandiyl-(5,12-dihydro-5,7,12,14-tetraazapentacene)]

3.83 g (10 mmol) N,N'-bis(2-aminophenyl)-1,12-diaminododecane is dissolved in 50 ml glacial acetic acid, and 1.68 g (10 mmol) dimethoxyquinone are added. The mixture is heated for reflux under argon for three hours, whereafter it is evaporated down to dryness. The darkblue crystalline mass is treated with 50 ml 10% ammonia solution and washed thoroughly with water followed by 25 ml acetone. The product is then thorougly dried under vacuum. Yield 3.90 g (100%).

EXAMPLE 2

0.4 g of the fluoroindine polymer prepared in Example 1 is dissolved in 10 ml chloroform and coated by "spincoating" on a glass plate (50 times 50 times 1.1 mm) with an indiumtinoxide coating presenting a conductivity of 30 ohm on the surface.

The properties of the electrochromic film is determined by placing said film in an electrochemical cell configuration, in which the glass plate represents one side of the cell, and where a transparent counterelectrode of indiumtinoxide on glass and a standard calomel electrode as reference electrode are used. The cell is filled with 0.5M sulphoric acid, and the electrodes are connected to a potentiostat, whereafter the film is examined by cyclic, electrical voltammetry being a method of determining the electrochemical properties of electroactive materials, including their oxidation and reduction potentials.

Figure 1:
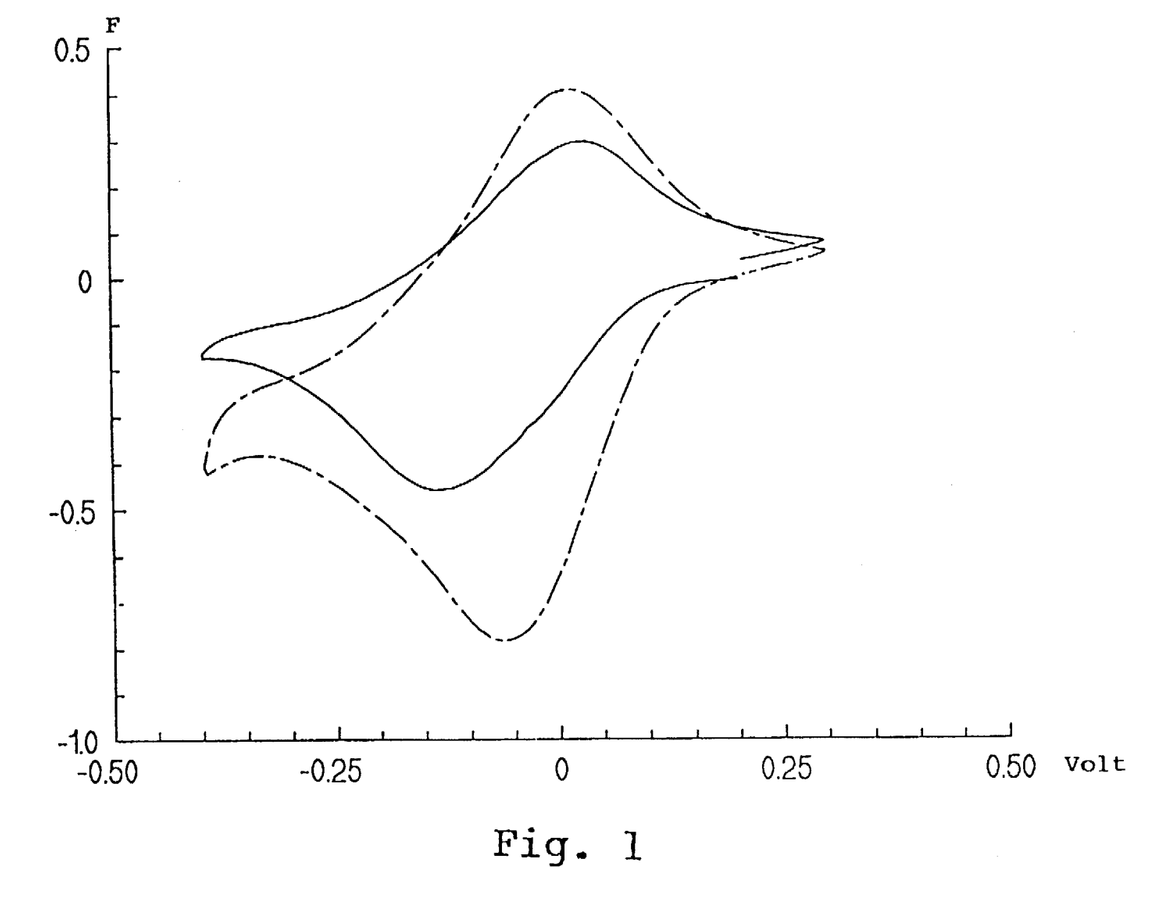
FIG. 1 illustrates by means of a voltammogram the reversible redox properties of a film produced from the fluoroindine polymer prepared in Example 1, determined as described in Example 2.

The resulting cyclic voltammogram appears from FIG. 1 and shows on the X-axis the potential difference between the reference electrode and the film, whereas the Y-axis indicates the current at the potential in question. The solid line indicates the course when the potential is changed by 1 mV per second, whereas the dotted line indicates the progress at 10 mV per scond. During the measuring, the cell is subjected to an oxidation and reduction cyclus, where the potential is initially varied from +0.25 V to −0.25 V and subsequently back to +0.25 V.

The symmetrical shape of the voltammetric curve indicates that it is a question of a reversible reaction, and it appears that the oxidation and the reduction take place at a potential of approximately −0.1 V relative to the calomel electrode. This is a fine position within the stability window of approximately ±1 V relative to the calomel electrode which is defined by reduction of oxygen and oxidation of water, respectively.

Figure 2:
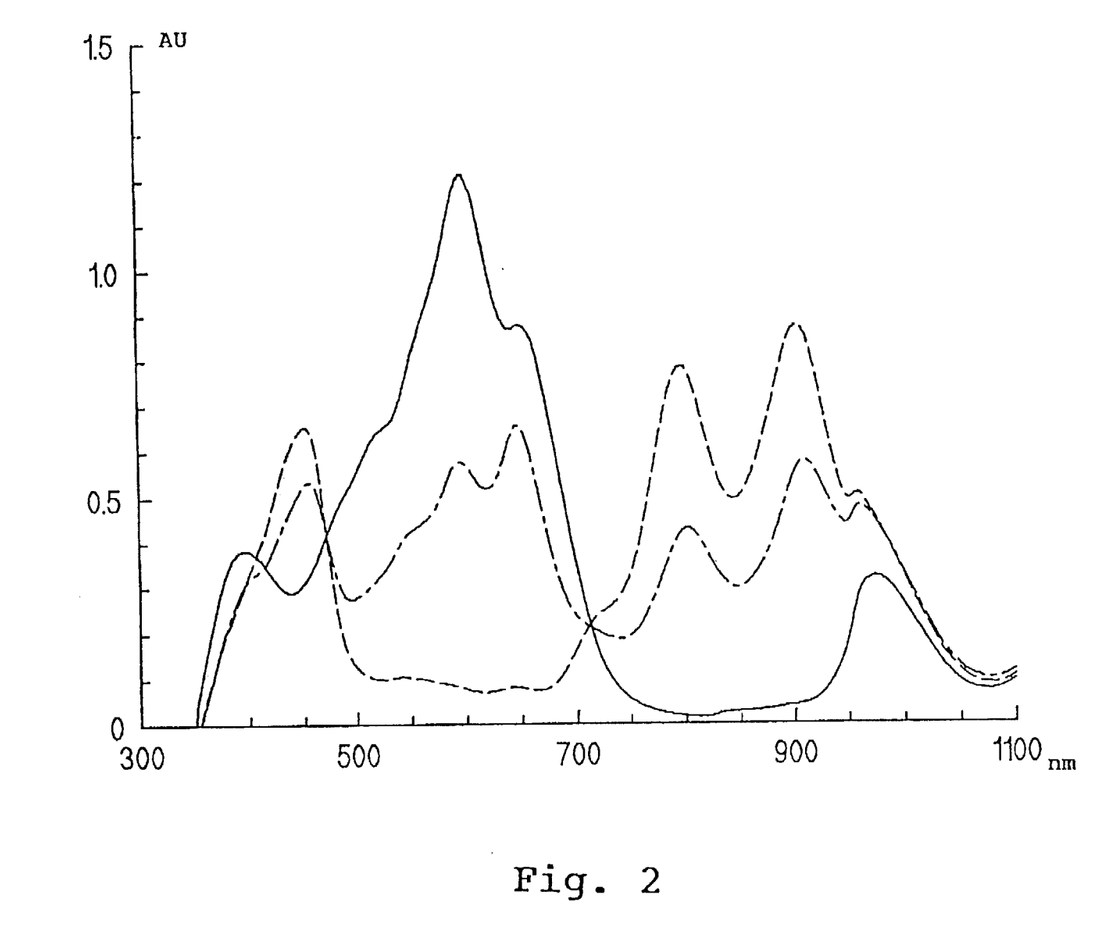
FIG. 2 illustrates the absorption versus the wavelength of the same film.

In addition, the spectroscopic properties at various potentials are examined by the electrochemical cell being placed in a spectrophotometer, and by the optical spectrum being recorded at various predetermined potentials. The absorption in absorption units (AU) versus the wavelength appears from FIG. 2. The solid line is the absorption at +200 mV, the dot-and-dash line at 0 mV, and the dotted line at −400 mV. It appears from the results, that the material reveals heavy absorptions in the area 550 to 700 nm at a potential of 200 mV relative to the calomel electrode which corresponds to a strong blue colour unlike the material almost not absorbing light in the same area at a potential of −400 mV, in which state the material has a very weak yellow colour (almost colourless).

EXAMPLE 3 (METHOD A)

The present Example illustrates the preparation of a material according to the invention by the following reaction course:

a) N-butyl-2-nitroaniline 17.3 g (0.110 mol) 2-chloro-nitrobenzene and 20 ml (14.8 g, 0.29 mol) butylamine are heated to boiling under reflux for four hours. During the cooling, the reaction mixture solidifies into an orange crystal mass, and 50 ml water and 20 ml diluted hydrochloric acid are added. An extraction is carried out with three times 50 ml $CHCl_3$. The entire organic phase is dried over $MgSO_4$, filtered, and evaporated to an orange oil. A distillation is performed by oil pump vacuum (approximately 1 mm Hg). After an initial fraction at 60° to 125° C., the product is distilled at 155° to 158° C./1 mm Hg. Yield: 11.24 g (57.9 mmol corresponding to 52.6%) N-butyl-2-nitroaniline.

b) N-butyl-2-aminoaniline 11.24 g (57.9 mmol) N-butyl-2-nitroaniline in 50 ml concentrated hydrochloric acid are cooled on ice bath to approximately 50° C., whereafter 50 g (0.22 mol) $SnCl_2$. $H_2O$ in 72 ml concentrated HCl are added. The relatively exothermal process causes the temperature to rise to approximately 70° C. The ice bath is removed when the temperature is approximately 60° C., and a stirring is performed at this temperature for approximately 30 minutes while a slightly pink solution is being formed.

By cooling on ice bath at a temperature ≧60° C., 85 g NaOH in 100 ml water are added. Towards the termination of the addition, $SnO_2$ is precipitated and is dissolved by further addition. The resulting product is partially precipitated, and the cooled suspension is exctracted twice by 150 ml ether. The entire organic phase is dried for a short period over granulated $CaCl_2$ and evaporated to a clear almost colourless oil which crystallizes. Yield: 8.8 g (53.6 mmol, approximately 93%) N-butyl-2-aminoaniline.

c) 5,12-Dibutyl-5,12-dihydro-5,7,12,14-tetraazapentacene 1.65 g (10 mmol) N-butyl-2-aminoaniline and 0.84 g (5 mmol) 2,5-dimethoxybenzoquinone i 50 ml glacial acetic acid are heated to boiling under reflux for three hours followed by evaporation to dryness. The darkblue powder is treated with 50 ml 10% ammonia solution and washed thoroughly with water, ethanol, and acetone (10 ml). After a thorough drying under vacuum, 1.95 g (95%) 5,12-dibutyl-5,12-dihydro-5,7,12,14-tetraazapentacene is obtained.

EXAMPLE 4

0.2 g 5,12-dibutyl-5,12-dihydro-5,7,12,14-tetraazapentacene is dissolved in 10 ml chloroform and spincoated on a polyethylene terephthalate film coated with indiumtinoxide with a surface resistance of 60 ohm.

The colour-changing properties of the film were determined in an electrochemical cell configuration with the coated film as one side of the cell and a transparent counter-electrode of indiumtinoxide on glass as well as with a standard calomel electrode as reference electrode. The measurings were performed in the same manner as in Example 2. The cyclic voltammogram and the spectrophotometric measurings showed properties of the film corresponding to the properties observed of the film examined in Example 2.

By the reversible process, the colour of the film changes from slightly yellow in the oxidized form to darkblue in the reduced form.

EXAMPLE 5 (METHOD B)

a) 2,3-Diaminophenacine 5 g o-phenylendiamine is dissolved in 150 ml 10% acetic acid and over a period of approximately 15 minutes 28 g $FeCl_3 \cdot 6H_2O$ in 50 ml water are added. The reaction mixture was left for two hours at room temperature. The resulting red crystals are filtered off and washed with approximately 25 ml water. A suspending is performed in approximately 200 ml water, and pH is set to approximately 13 by addition of NaOH, whereafter the resulting yellow product is filtered off and washed with water and ethanol. The product is suspended in 100 ml boiling ethanol, cooled, and filtered, whereafter a washing is performed with a small amount of ethanol and petroleum ether. Yield: 2.3 g 2,3-diaminophenacine.

b) 2-Carboxy-5,12-dihydro-5,7,12,14-tetraazapentacene 0.5 g 2,3-diaminophenacine and 0.5 g o-diaminobenzoic acid are mixed with 5 g benzoic acid and heated to 250° C. by means of a heat gun for 10 minutes. Upon cooling, the reaction mixture is slowly mixed with boiling ethanol containing a small amount of concentrated HCl to form the hydrochloride of the dihydrotetraazapentacene at the same time as most of the benzoic acid is thereby removed. The product is filtered off and washed with additional ethanol and with diluted HCl. Upon drying, other side products are removed by sublimation for a few minutes at 250° C./0.1 mm Hg. The remaining violet-blue powder is pure 2-carboxy-5,12-dihydro-5,7,12,14-tetraazapentacene. Yield: 0.2 g.

A coated film produced in the same manner as in Example 4 shows corresponding electrochemical properties. The electrochromic compounds are, however, sligthly water-soluble and are therefore more suited for use in non-aqueous structures.

EXAMPLE 6 (METHOD C)

Poly[5,12'-ω-(3,6-dioxaoctandiyl)-5,12-dihydro-5,7,12,14-tetraazapentacene]

-continued a) N,N'-bis(2-nitrophenyl)-1,8-diamino-3,6-dioxaoctane 2-nitrochlorobenzene (44 g, 179 mmol) and 19.7 g (133 mmol) 1,8-diamino-3,6-dioxaoctane are mixed and heated to approximately 130° C. with the result that an exothermal reaction occurs, where the temperature of the reaction mixture rises to 190° C. in five minutes with some development of gas. The reaction flask is removed from the oil bath, and while the reaction mixture solidifies quickly 25 ml xylene are admixed in order to maintain the possibility of stirring the reaction mixture. When the reaction temperature has dropped to 110° C., the reaction mixture is again heated in oil bath to 170° C. for 90 minutes, whereafter a cooling and addition of 100 ml $CH_2Cl_2$ and 100 ml water are performed. The $CH_2Cl_2$-phase is evaporated into an orange oil which is then poured into 100 ml water, and by way of seeding a solid mass crystallizes. A filtration is performed, and the filter is washed with approximately 300 ml water. The moist orange-coloured product is recrystallized from 300 ml 99% ethanol. Yield: 33.9 g (86.8 mmol, 65.3%) N,N'-bis(2-nitrophenyl)-1,8-diamino-3,6-dioxaoctane.

b) N,N'-bis(2-aminophenyl)-1,8-diamino-3,6-dioxaoctane 26.1 g N,N'-bis(2-nitrophenyl)-1,8-diamino-3,6-dioxaoctane is dissolved in 100 ml concentrated HCl and stirred while 92.5 g $SnCl_2$ dissolved in 100 ml concentrated HCl are added during approximately two minutes. The reaction is exothermal and the temperature rises to 90° C. at the same time as the colour changes from light orange through dark to light green, whereafter a product starts to precipitate. After one hour the reaction mixture is cooled on an ice bath. The crystalline product is filtered off and dissolved in 150 ml water and added to 50 g NaOH in 300 ml ice water. A greenish oil is separated. The product is extracted with 100+50 ml $CH_2Cl_2$, dried over $MgSO_4$, and evaporated under vacuum. Yield: 21.7 g (57.9 mmol, N,N'-bis(2-aminophenyl)-1,8-diamino-3,6-dioxaoctane.

c) Poly[5,12'-ω-(3,6-dioxaoctandiyl)-5,12-dihydro-5,7,12,14-tetraazapentacene]

2.6 g (6.7 mmol) N,N'-bis(2-aminophenyl)-1,8-diamino-3,6-dioxaoctane are dissolved in 50 ml acetic acid, and 1.13 g dimethoxyquinone are added. The mixture is heated to boiling under reflux for three hours, and the reaction mixture turns darkblue. The acetic acid is distilled off, and the solid product is washed with water and ethanol. The product is thoroughly dried under vacuum. Yield: 2.78 g violet powder of the polymeric tetraazapentacene stated in the headline. The electrochemical properties correspond exactly to the properties of the fluoroindine polymer produced according to Example 1 as described in Example 2.

EXAMPLE 7 (BATTERY)

0.4 g of the fluoroindine polymer prepared in Example 1 was dissolved in 10 ml chloroform and coated on a thin nickel film by an immersing process. A solid-state battery is produced from the coated film by coating the film with a propylene carbonate solution of polyethylene glycol (20%) and lithium perchlorate (5%). After drying under oxygen-free and steam-free conditions in a glove box, the battery was closed by a carbon film impregnated with 10% metallic lithium. The resulting lihtium-fluoroindine battery operates by the charge being released at a simultaneous reduction of the fluoroindine layer and dissolving of lithium. The process is reversible, and when completely charged the rechargeable battery provides a potential difference of 2.9 V, whereas the potential only drops to approximately 2.5 V in connection with a discharging. The battery presents a density of charge of 300 Wt/kg in the active layer. By way of comparison the maximum theoretical density of charge of a lead battery is 180 Wt/kg, and in a nickel-cadmium battery 200 Wt/kg.

EXAMPLE 8 (LAMINATED ELECTROCHROMIC UNIT)

0.4 g of the fluoroindine polymer produced in Example 1 is dissolved in 10 ml chloroform, and 0.2 g polystyrene (molar weight 250,000) is added. This solution is spincoated on a 100 μm thick polyethylene terephthalate film (PET) with an indiumtinoxide coating of a specific surface resistance of 60 ohm. The film is subsequently reduced under argon by immersion in a 1M hydrochloric acid solution containing SnCl$_2$. After a short rinsing with clean water, the film is spincoated with an aqueous solution of phosphoric acid (30%) and polyethylene imine (molar weight approximately 125,000) (9%).

After a complete evaporation of the water content, the coated film is carefully laminated with PET-film with indiumtinoxide as stated above, here additionally coated with a 3 μm layer of wolframoxide (WO$_3$). The coating is performed by way of cathodic atomization under vacuum (vacuum sputtering). The resulting flexible electrochromic laminate presents in the resulting form an almost colourless transparency, slightly yellow, and it can be reversibly converted into a strong blue form by applying a potential difference of 0.5 V between the two indiumtinoxide layers.

It is obvious from the above description of the invention that it can be varied in many ways. Such variations are not to be considered deviations from the scope and idea of the invention, and all such modifications obvious to persons skilled in the art are also to be considered comprised by the following claims.

In the present description and the claims % means % by weight unless other indications are found.

We claim:

1. Stable, electroactive material which when a potential is applied from the outside is subjected to one or more reversible redox reactions, for use in devices with an electrochromic display or another electrochromic colour change or in batteries, characterised by containing at least one condensed ring structure I of one of the formulas I red or I ox in the redox reaction equation:

in which the groups X, which may be identical or different, are O, S or NR$_3$, at least one of the groups being NR$_3$, where the structures A, which may be identical or different, may be any molecular structure not blocking the redox reaction, and, optionally, may carry one or more identical or different substituents R$_4$,
where R$_1$, R$_2$, R$_3$, and R$_4$, which may be identical or different, may be any substituent not blocking the redox reaction, and where one or more of the substituents R$_1$, R$_2$, R$_3$, and R$_4$ may also form part of a linker residue L, which is attached to one or more additional ring structures I, and where L is a divalent or polyvalent group not blocking the redox reaction.

2. Electrochromic material as claimed in claim 1, characterised by both groups X being NR$_3$.

3. Electroactive material as claimed in claim 1, characterised in that one or more of the groups R$_1$, R$_2$, R$_3$, and R$_4$, which may be identical or different, are a straight or branched chain group with 1 to 24 chain atoms selected among C, O, N, S, and Si.

4. Electroactive material as claimed in claim 1 or 2 or 3, characterised in that one or more of the groups R$_1$, R$_2$, R$_3$, and R$_4$, which may be identical or different, are alkyl with 1 to 18 carbon atoms, thioalkyl with 1 to 18 carbon atoms, and 1 to 6 sulphur atoms, oxoalkyl with 1 to 18 carbon atoms, and 1 to 6 oxygen atoms, nitro, halogen, phenyl, alkenyl with 1 to 18 carbon atoms, cyano, hydroxy, alkoxy with 1 to 6 carbon atoms or alkylamino with 1 to 6 carbon atoms.

5. Electroactive material as claimed in claim 1, characterised in that one or both structures A comprise a carbocyclic or heterocyclic ring condensed with ring No. 1 and/or ring No. 3, respectively, in the structure I.

6. Electroactive material as claimed in claim 5, characterised in that the carbocyclic or heterocyclic ring is aromatic.

7. Electroactive material as claimed in claim 1, characterised in that it is an oligomeric or polymeric material, in which the ring structure I forms part, where the polymeric structure results from linker residues L.

8. Electroactive material as claimed in claim 7, characterised in that the linker residues L are straight chained or branched, divalent or polyvalent groups with 3 to 150 chain atoms selected among C, O, N, S, and Si.

9. Electroactive material as claimed in claim 7 or 8, characterised in that the linker residues are derived from one or more precursor materials (monomer or prepolymer) selected among precursor materials to polyalkene, polyether, polysulphide, polyamine, silicone or mixtures thereof.

10. A method for the preparation of a stable electroactive material in form of a compound containing a condensed ring structure I of the formula shown in claim 1, in which the groups X, which may be identical or different, are O, S or NR$_3$, and where A, R$_1$, R$_2$, R$_3$, and R$_4$ may have any meaning indicated in claim 1, with the proviso that none of the substituents R$_1$, R$_2$, R$_3$, and R$_4$ can form part of a linker residue L attached to additional ring structures characterised by a) reacting an amine of the formula II where A and X have the meanings stated above, with a quinone of the formula III where R$_1$ and R$_2$ have the meanings stated above, and Q$_1$ is hydrogen or C$_{1-4}$alkyl, or b) for the preparation of compounds of the ring structure Ib, in which Ib ox has the formula in which R$_3$ and A have the meanings stated above, where R$_a$ and R$_b$ may have the same meaning as the groups R$_1$, R$_3$, and R$_4$, and where each of the two groups R$_{a/b}$ is the same as R$_a$ and R$_b$, respectively, reacting 2 molecules of an o-phenylene diamine of the formula IV

IV in which $R_a$ and $R_b$ have the meanings stated above, in the presence of an oxidation agent to form a compound of the formula V

V in which $R_a$, $R_b$, and $R_{a/b}$ have the meanings stated above, and then reacting the compound of the formula V with a compound of the formula VI

VI in which $R_3$ and A have the meanings stated above.

11. A method for the preparation of a stable electroactive material as claimed in claim 1 in form of an oligomeric or polymeric material containing several ring structures I, in which X, A, $R_1$, $R_2$, $R_3$, and $R_4$ have the meanings stated in claim 1, and in which one or more linker residues L having the meaning sated in claim 1 form part, characterised by
c) for the preparation of an electroactive polymeric material of the following structure IC ox in which A, $R_1$, $R_2$, and L have the meanings stated above, and n is the polymerisation degree, reacting a compound of the formula VII

VII in wich A has the meaning stated in claim 1, and $Q_2$ is a leaving group, with a diamine compound of the formula

$$H_2N\text{-}L\text{-}NH_2$$ VIII where L has the meaning stated in claim 1, to form a compound of the formula IX

IX where A and L have the meaning stated above, reducing the compound of the formula IX to obtain a compound of the formula X

X in which A and L have the meanings stated above, and reacting the compound of formula X with a quinone of the formula III

III in which $R_1$ and $R_2$ have the meanings stated above, and $Q_1$ is hydrogen or $C_{1-4}$alkyl, or d) for the preparation of a polymeric, electroactive material with the structure Id, where Id ox has the structure in which $R_1$, $R_2$, $R_3$, and L have the meanings stated above, n is the polymerization degree and $A_1$ is a structure A comprising a benzene ring, reacting a compound of the formula XI in which $A_1$ has the meaning stated above, and $Q_3$ is a protecting group, with a diamine compound of the formula VIII

VIII in which L has the meaning stated above, to obtain a compound of the formula XII in which $A_1$, L, and $Q_3$ have the meanings stated above, nitrating the rings $A_1$ in the o-position into the groups $NHQ_3$ in the compound of the formula XII, and in arbitrary sequence or simultaneously reducing the nitro groups and removing the protecting groups $Q_3$ to form a compound of the formula XIII in which $A_1$ and L have the meanings stated above, and reacting the compound of the formula XIII with a compound of the formula III in which $R_1$, $R_2$, and $Q_1$ have the meanings stated above, to form a polymeric compound with the structure Id, in which $R_3$ is hydrogen and, optionally, as termination or at a suitable stage during the synthesis converting one or more hydrogen groups $R_3$ into $R_3$-groups having another of the meanings stated for $R_3$, or e) for the preparation of a polymeric structure Ie, in which Ie ox is of the formula in which A, R1, L and n have the meanings stated above reacting a compound of the formula XIV in which A, $R_1$, and $R_2$ have the meanings stated in claim 1, with a compound of the formula XV

XV in which $Q_4$ is a leaving group.

* * * * *